(12) United States Patent
Freeman

(10) Patent No.: US 6,701,939 B2
(45) Date of Patent: Mar. 9, 2004

(54) DENTAL DEVICE FOR CLEANING BETWEEN TEETH

(76) Inventor: Roger J. Freeman, 7618 W. 59th St. Terrace, Overland Park, KS (US) 66202

( * ) Notice: Subject to any disclaimer, the term of this patent is extended or adjusted under 35 U.S.C. 154(b) by 8 days.

(21) Appl. No.: 10/076,197

(22) Filed: Feb. 13, 2002

(65) Prior Publication Data

US 2003/0152887 A1 Aug. 14, 2003

(51) Int. Cl.$^7$ .............................................. A61C 15/00
(52) U.S. Cl. ...................................... 132/321; 132/329
(58) Field of Search ................................... 132/321, 329

(56) References Cited

U.S. PATENT DOCUMENTS

| | | | |
|---|---|---|---|
| 3,978,872 A | 9/1976 | Bond | 132/329 |
| 4,159,182 A | 6/1979 | Adolfson | 366/343 |
| 4,271,854 A | 6/1981 | Bengtsson | 132/329 |
| 4,660,583 A * | 4/1987 | Brown | 132/329 |
| 4,800,905 A * | 1/1989 | Stuart | 123/321 |
| 4,875,496 A | 10/1989 | Prabhudass | 132/329 |
| D333,534 S | 2/1993 | Dizon | D28/64 |
| 5,234,009 A | 8/1993 | Lemon et al. | 132/329 |
| D345,825 S | 4/1994 | Arnold | D28/64 |
| D367,545 S | 2/1996 | Burke | D28/64 |
| 5,588,452 A | 12/1996 | Granger | 132/321 |
| 5,735,300 A | 4/1998 | Higgins | 132/329 |
| 5,769,103 A | 6/1998 | Turjak | 132/329 |
| 6,012,468 A | 1/2000 | Huang | 132/321 |
| 6,044,848 A | 4/2000 | Huang | 132/321 |
| D437,459 S | 2/2001 | Inaba | D28/65 |
| 6,213,132 B1 | 4/2001 | Andrews | 132/321 |

* cited by examiner

Primary Examiner—John J. Wilson
(74) Attorney, Agent, or Firm—Hovey Williams LLP

(57) ABSTRACT

A dental device (10) broadly comprises a center section (12) flanked by a first picking section (14) and a second picking section (16). The first picking section (14) and the second picking section (16) are relatively flat and may include a roughened surface (50). The device (10) is preferably constructed in one-piece and molded from semi-rigid thermoplastic which resists breaking. The first picking section (14) is thicker and stronger than the second picking section (16) in order to dislodge most any debris caught between teeth. The second picking section (16) is narrow enough to reach between closely spaced teeth. In use, a person holds the device (10) by the center section (12) and inserts either picking section (14,16) between their teeth. The person works the device (10) back and forth using the roughened surface (50) or angles of either section (14,16) to disturb bacteria and other foreign substances.

6 Claims, 3 Drawing Sheets

DENTAL DEVICE FOR CLEANING BETWEEN TEETH

BACKGROUND OF THE INVENTION

1. Field of the Invention

The present invention relates to oral hygiene tools. More particularly, the present invention relates to a dental device that can be used instead of dental floss, a traditional toothpick, or a toothbrush to disturb food, bacteria, and other foreign substances between teeth.

2. Description of Prior Art

Oral hygiene is an important concern. Food, bacteria, and other foreign substances can become lodged between and otherwise stick to a person's teeth after eating and unless removed, can cause formation of plaque and damage to the person's teeth, gums, and mouth. Therefore, it is necessary to disturb such substances between teeth.

There are currently three common types of oral hygiene tools used to disturb bacteria. A first type, toothbrushes, are widely used and are often used exclusively of all other tools. While toothbrushes are effective for disturbing bacteria and other foreign substances on front and rear surfaces of teeth, they are largely ineffective for disturbing bacteria and other foreign substances between teeth. This is because a typical toothbrush comprises a plurality of similar length bristles. While one or more bristles are positioned adjacent a gap between teeth several other bristles are in contact with adjacent teeth, thereby preventing bristles from entering the gap and disturbing bacteria and other foreign substances in the gap.

In order to push these bristles into the gap a person must exert more force on the handle of the toothbrush. Exerting more force may cause some bristles to enter the gap; however, other bristles may pierce the person's gums which only makes the person's mouth more susceptible to the effects of bacteria.

Another common type of oral hygiene tool is dental floss. While dental floss can be an effective tool for disturbing bacteria between teeth, dental floss has significant drawbacks. For instance, dental floss must be thin in order to fit between closely spaced teeth and therefore often breaks. Additionally, use of dental floss requires a person to look into a mirror, grip the dental floss with two hands, and put their fingers into their mouth. This is inconvenient, awkward, and can introduce bacteria to the rest of the person's mouth while trying to disturb bacteria between teeth. Finally, dental floss cannot be used if a person is wearing braces because braces typically include a wire or other structure that prevents dental floss from reaching into gaps between teeth.

A final common type of oral hygiene tool is a toothpick. Toothpicks typically have opposed picking sections or points joined by a larger central gripping section that permits the toothpick to be held and that lends strength to the picking sections.

Each picking section often comprises an abrupt curved or slanted region. The abrupt region limits how far the toothpick can reach between teeth. In other cases, each picking section has gradually slanted sides. Slanted sides also limit how far a toothpick can reach between teeth. Additionally, if a toothpick includes slanted sides sufficient to allow a picking section to fit between teeth, it often includes a sharp point. Sharp points can pierce gums, making a mouth more susceptible to the effects of bacteria.

Another disadvantage of many toothpicks is that they are made from wood. Wood is a highly porous material which can sustain bacteria and therefore introduce bacteria into a mouth. Wood is also susceptible to splitting, which may leave wood fragments between teeth. Split wood can also have a sharp point, which can pierce gums, making a mouth more susceptible to the effects of bacteria.

Accordingly, there is a need for an improved dental device to disturb bacteria and other foreign substances between teeth that overcomes the limitations of the prior art.

SUMMARY OF THE INVENTION

The dental device of the present invention overcomes the above-identified problems and provides a distinct advance in the art of oral hygiene tools. More particularly, the present invention provides a dental device that more easily fits between teeth so that it can be used instead of dental floss or a traditional toothpick to disturb bacteria and other foreign substances between teeth.

The preferred dental device broadly comprises a center section flanked by a first picking section and a second picking section. The center section may be gripped to position one of the picking sections between two adjacent teeth for disturbing bacteria and other foreign substances between the teeth.

The first picking section is generally flat and includes two sides, two edges, a tip, and a base. The sides meet the edges and the tip at approximately ninety degree angles. These angles are sharp enough to disturb bacteria on a person's teeth while not sharp enough to pose a risk of cutting the person's gums.

The tip includes two corners transitioning between the tip and the edges. The corners are rounded and act as a safety feature to prevent the person from piercing or scraping their gums.

The second picking section includes two sides, two edges, a tip, and a base and is similar to the first picking section. The most significant difference between the second picking section and the first picking section is that the second picking section is thinner and more flexible than the first picking section so that it more easily fits between closely spaced teeth.

The picking sections may include roughened surfaces. The roughened surfaces help loosen bacteria and massage gums.

The device is preferably constructed in one-piece and molded from semi-rigid thermoplastic. The thermoplastic gives the first picking section sufficient rigidity to dislodge most any debris caught between teeth. The thermoplastic also gives the second picking section sufficient flexibility to reach between teeth and around braces. Additionally, the thermoplastic resists breaking, thereby preventing leaving fragments between teeth or presenting a sharp point. Furthermore, the thermoplastic is not porous and resists retaining bacteria and other foreign substances. Finally, the thermoplastic is easily cleaned, which allows the device to be cleaned and reused repeatedly.

In use, a person holds the device by the center section and inserts the first picking section into gaps between their teeth. The person works the device back and forth in each gap using the roughened surfaces or angles of the first picking section to disturb bacteria and other foreign substances. The person can also rotate the device back and forth along a longitudinal axis. When necessary, the person can insert the second picking section between narrower gaps, thereby reaching areas unreachable with the first picking section.

BRIEF DESCRIPTION OF THE DRAWINGS

A preferred embodiment of the present invention is described in detail below with reference to the attached drawing figures, wherein.

DETAILED DESCRIPTION OF A PREFERRED EMBODIMENT

Figure 1:
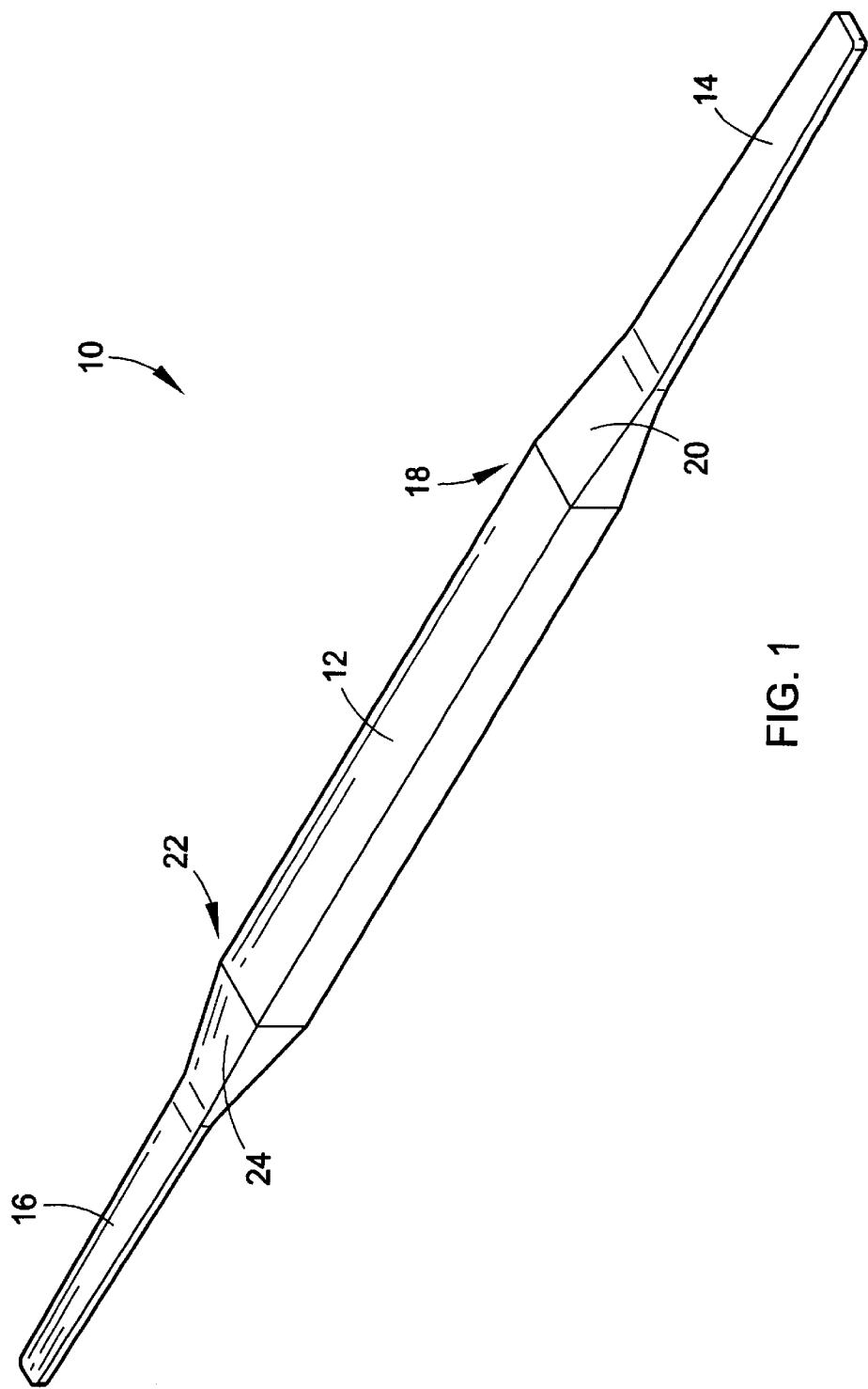
FIG. 1 is a perspective view of a dental device constructed in accordance with a first embodiment of the present invention.

Referring to FIG. 1, a dental device 10 constructed in accordance with a first embodiment of the invention broadly comprises a center section 12 flanked by a first picking section 14 and a second picking section 16. The center section 12 is approximately sixty thousands of an inch thick, approximately one tenth of an inch wide, and approximately one inch long. The center section 12 retains its thickness and width throughout its length. The center section 12 is wider than it is thick allowing a person to properly align the device 10 without needing to look at the device 10. The center section 12 may be elliptical, rectangular, oblong, or any other shape that can assist the person in aligning the device 10 without having to look at the device 10.

Adjoined to a first end 18 of the center section 12, is a first transition 20. The first transition 20 converges from the center section 12 to the first picking section 14 in its approximately one hundred and eighty-eight thousands of an inch length.

Similarly, adjoined to a second end 22 of the center section 12, is to a second transition 24. The second transition 24 converges from the center section 12 to the second picking section 16 in its approximately one hundred and eighty-eight thousands of an inch length.

Figure 3:
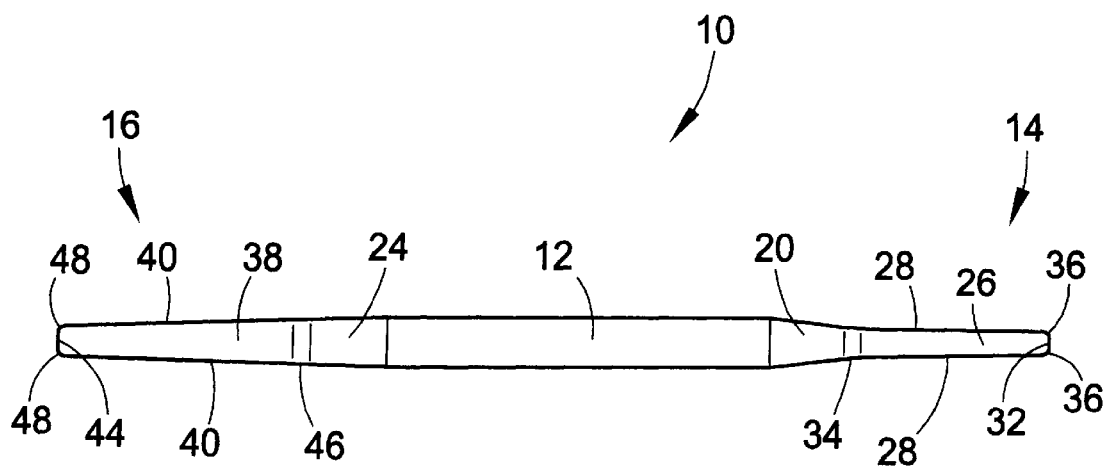
FIG. 3 is a plan view of the dental device of FIG. 1.

Also referring to FIG. 3, the first picking section 14 includes two sides 26, two edges 28, a tip 32, and a base 34. The first picking section 14 is approximately sixteen thousands of an inch thick and approximately five hundred and sixty-three thousands of an inch long. The first picking section 14 is approximately fifty-five thousands of an inch wide at the tip 32 and continuously widens to an approximately ninety thousands of an inch width at the base 34, where it adjoins the first transition 20.

The sides 26 meet the edges 28 and the tip 32 at approximately ninety degree angles. These angles are sharp enough to disturb bacteria on the person's teeth while not sharp enough to pose a risk of cutting the person's gums.

The tip 32 includes two corners 36 transitioning between the tip 32 and the edges 28. The corners 36 are rounded to approximate a circle with a ten thousands of an inch radius. The corners 36 act as a safety feature to prevent the person from piercing or scraping his or her gums.

The second picking section 16 includes two sides 38, two edges 40, a tip 44, and a base 46. The second picking section 16 is approximately eleven thousands of an inch thick and approximately four hundred and thirty-eight thousands of an inch long. The second picking section 16 is approximately fifty thousands of an inch wide at the tip 44 and continuously widens to an approximately sixty-five thousands of an inch width at the base 46, where it adjoins the second transition 24.

The sides 38 meet the edges 40 and the tip 44 at approximately ninety degree angles. These angles are sharp enough to disturb bacteria on the person's teeth while not sharp enough to pose a risk of cutting the person's gums.

The tip 44 includes two corners 48 transitioning between the tip 44 and the edges 40. The corners 48 are rounded to approximate a circle with a ten thousands of an inch radius. The corners 48 act as a safety feature to prevent the person from piercing or scraping his or her gums.

Figure 4:
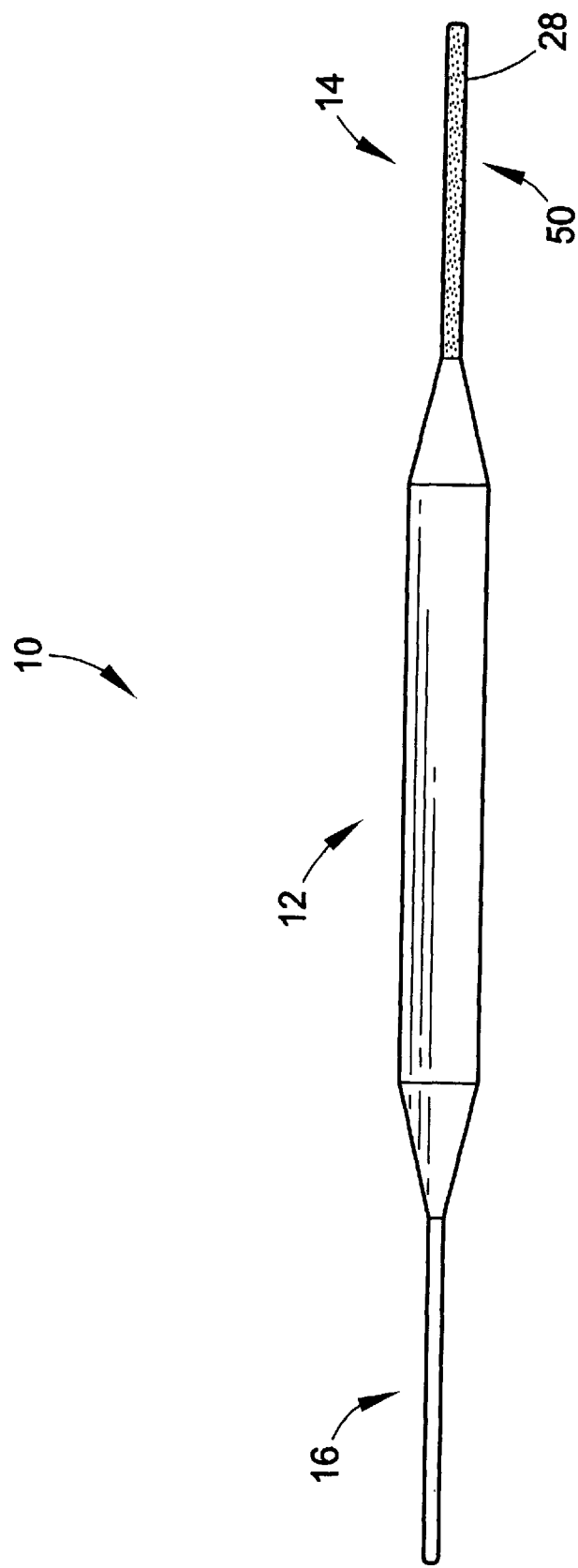
FIG. 4 is a side elevation view of the dental device of FIG. 2 showing a roughened surface on an edge of a first picking section.

Also referring to FIG. 4, the picking sections 14,16 may include roughened surfaces 50. While the roughened surfaces 50 may be any of the sides 26,38, edges 28,40, and/or tips 32,44, a preferred embodiment comprises the roughened surfaces 50 on the edges 28,40. The roughened surfaces 50 help loosen bacteria and massage gums.

The device 10 is preferably constructed in one-piece and molded from semi-rigid thermoplastic. The thermoplastic gives the first picking section 14 sufficient rigidity to dislodge most any debris caught between teeth. The thermoplastic also gives the second picking section 16 sufficient flexibility to reach between teeth and around braces. The second picking section 16 is also thin enough to fit into narrow gaps between closely spaced teeth. Additionally, the thermoplastic resists breaking, thereby preventing leaving fragments between teeth and presenting a sharp point. Furthermore, the thermoplastic is not porous, and therefore resists retaining bacteria and other foreign substances. Finally, the thermoplastic is easily cleaned, which allows the device 10 to be cleaned and reused repeatedly.

Figure 2:
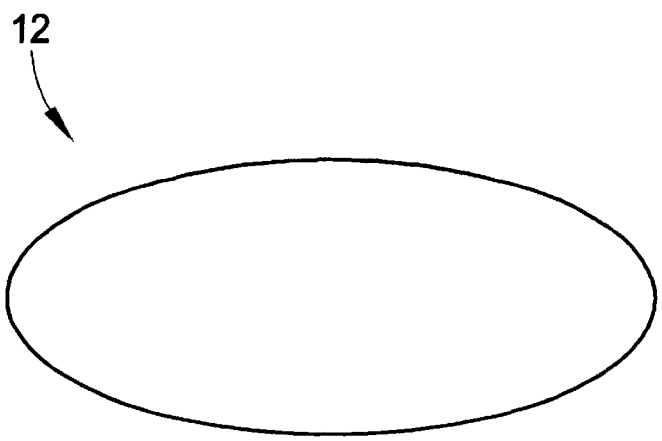
FIG. 2 is a cross-section of a center section of a dental device constructed in accordance with a second embodiment of the present invention.

FIG. 2 shows the center section 12 of a second embodiment with an elliptical cross-section. The elliptical cross-section is preferred, since it allows a person to easily, comfortably, and quickly rotate the device 10 along its longitudinal axis controlling the alignment the device 10. Rotating the device 10 allows the person to control the orientation of the picking sections 14,16 as the device 10 is worked back, forth, up, and down in gaps between the person's teeth.

In a third embodiment, the picking sections 14,16 may have a slightly tapered thickness. The slightly tapered thickness may be included in order to, for example, strengthen the picking sections 14,16. While the slightly tapered thickness may lend strength, it may limit how far each picking section 14,16 may be inserted between teeth. This may limit the usefulness of the device 10. Therefore, in the third embodiment, the picking section's 14,16 thickness may be constantly tapered up to five thousands of an inch along its length. For example, the first picking section 14 is described as approximately sixteen thousands of an inch thick. The first picking section 14 of the third embodiment may be approximately thirteen thousands of an inch thick at the tip 32 and approximately eighteen thousands of an inch thick at the base 34.

In a fourth embodiment, the picking sections 14,16 may have a constant width. The constant width may be included in order to, for example, strengthen the picking sections 14,16 or simplify manufacturing. While the constant width may lend strength, it may limit the usefulness of the device 10.

In use, a person holds the device 10 by the center section 12 and inserts the first picking section 14 into gaps between his or her teeth. The person works the device 10 into each gap using the roughened surfaces 50 or angles of the first picking section 14 to disturb bacteria and other foreign substances. The person can also rotate the device 10 back and forth along its longitudinal axis. When necessary, the person can insert the second picking section 16 between narrower gaps, thereby reaching areas unreachable with the first picking section 14.

It can be seen, that the device 10 includes a sturdy center section 12 that allows the person to use the device 10 without putting their fingers into their mouth. Additionally, the device 10 transitions from the center section 12 to picking sections 14,16 abruptly, allowing for relatively long picking sections 14,16. The picking sections 14,16 are therefore able to reach deep between teeth and behind braces.

While the present invention has been described above, it is understood that other materials and/or dimensions can be substituted. These and other minor modifications are within the scope of the present invention.

For example, the center section 12 may be between thirty thousands of an inch and one hundred thousands of an inch thick, up to one hundred thousands of an inch wider than it is thick, and between one half of an inch and two inches long. Additionally, each picking section 14,16 may be between five thousands of an inch and thirty-five thousands of an inch thick, between twenty thousands of an inch and one hundred and fifty thousands of an inch wide, and between one quarter of an inch and three quarters of an inch long. The transitions may also be between fifty thousands of an inch and two tenths of an inch long.

Having thus described a preferred embodiment of the invention, what is claimed as new and desired to be protected by Letters Patent includes the following:

1. A dental device for disturbing bacteria and other foreign substances between teeth, the device comprising:
   an elliptical center plastic gripping section having a first end and a second end, wherein the center section is between sixty thousands of an inch and eighty thousands of an inch thick, between thirty thousands of an inch and fifty thousands of an inch wider than it is thick, and between three quarters of an inch and one inch long;
   a first plastic transition section adjoined to the first end, wherein the first transition section is between one hundred and seventy-five thousands of an inch and two tenths of an inch long;
   a second plastic transition section adjoined to the second end, wherein the second transition section is between one hundred and seventy-five thousands of an inch and two tenths of an inch long;
   a first flat plastic picking section adjoined to the first transition section having a first tip and a first base, wherein the first picking section is between twelve thousands of an inch and twenty thousands of an inch thick, between forty-five thousands of an inch and one tenth of an inch wide, between one quarter of an inch and three quarters of an inch long, and the first picking section's width converges along its length such that the first tip is between thirty thousands of an inch and forty thousands of an inch narrower than the first base; and
   a second flat plastic picking section adjoined to the second transition section having a second tip and a second base, wherein the second picking section is thinner than the first picking section, is between seven thousands of an inch and fifteen thousands of an inch thick, between forty thousands of an inch and seventy-five thousands of an inch wide, between one quarter of an inch and three quarters of an inch long, and the second picking section's width converges along its length such that the second tip is between ten thousands of an inch and twenty thousands of an inch narrower than the second base.

2. The dental device as set forth in claim 1, wherein at least one picking section includes at least one roughened surface.

3. The dental device as set forth in claim 1, wherein at least one picking section includes at least one rounded corner.

4. A dental device for disturbing bacteria and other foreign substances between teeth, the device comprising:
   a center plastic gripping section having a first end and a second end, wherein the center section is between sixty thousands of an inch and eighty thousands of an inch thick, between thirty thousands of an inch and fifty thousands of an inch wider than it is thick, and between three quarters of an inch and one inch long;
   a first plastic transition section adjoined to the first end, wherein the first transition section is between one hundred and seventy-five thousands of an inch and two tenths of an inch long;
   a second plastic transition section adjoined to the second end, wherein the second transition section is between one hundred and seventy-five thousands of an inch and two tenths of an inch long;
   a first flat plastic picking section adjoined to the first transition section having a first tip and a first base, wherein the first picking section is between twelve thousands of an inch and twenty thousands of an inch thick, between forty-five thousands of an inch and one tenth of an inch wide, between one quarter of an inch and three quarters of an inch long, and the first picking section's width converges along its length such that the first tip is between thirty thousands of an inch and forty thousands of an inch narrower than the first base; and
   a second flat plastic picking section adjoined to the second transition section having a second tip and a second base, wherein the second picking section is thinner than the first picking section, is between seven thousands of an inch and fifteen thousands of an inch thick, between forty thousands of an inch and seventy-five thousands of an inch wide, between one quarter of an inch and three quarters of an inch long, and the second picking section's width converges along its length such that the second tip is between ten thousands of an inch and twenty thousands of an inch narrower than the second base.

5. The dental device as set forth in claim 4, wherein at least one picking section includes at least one roughened surface.

6. The dental device as set forth in claim 4, wherein at least one picking section includes at least one rounded corner.

* * * * *